(12) United States Patent
Benet et al.

(10) Patent No.: US 9,316,572 B2
(45) Date of Patent: Apr. 19, 2016

(54) DEVICE FOR MEASURING THE ACTIVITY OF A LIQUID IN A COMPLEX MEDIUM AND ASSOCIATED METHOD

(75) Inventors: Jean-Claude Benet, Juvignac (FR); Bruno Cousin, Nîmes (FR); Fabien Cherblanc, Montpellier (FR); Samuel Ouoba, Monptellier (FR)

(73) Assignees: Centre National de la Recherche Scientifique, Paris (FR); Universite Montpellier 2, Montpellier (FR)

( * ) Notice: Subject to any disclaimer, the term of this patent is extended or adjusted under 35 U.S.C. 154(b) by 624 days.

(21) Appl. No.: 13/508,169

(22) PCT Filed: Nov. 4, 2010

(86) PCT No.: PCT/FR2010/000734
§ 371 (c)(1),
(2), (4) Date: Jul. 11, 2012

(87) PCT Pub. No.: WO2011/055042
PCT Pub. Date: May 12, 2011

(65) Prior Publication Data
US 2012/0266663 A1    Oct. 25, 2012

(30) Foreign Application Priority Data
Nov. 4, 2009 (FR) ..................... 09 05293

(51) Int. Cl.
*G01N 7/14* (2006.01)
*G01N 3/08* (2006.01)

(52) U.S. Cl.
CPC .. *G01N 7/14* (2013.01); *G01N 3/08* (2013.01); *G01N 2203/0085* (2013.01)

(58) Field of Classification Search
CPC ....... G01N 7/14; G01N 17/002; G01N 25/56; G01N 2035/00356; G01N 2203/0222; G01N 2203/023; G01N 2291/02408; G01N 2291/02416
See application file for complete search history.

(56) References Cited

U.S. PATENT DOCUMENTS 2,534,718 A * 12/1950 Leas et al. ............... 73/38
3,239,880 A * 3/1966 Oxel ....................... 374/55
(Continued)

FOREIGN PATENT DOCUMENTS

| DE | 41 06 923 A1 | 9/1991 |
| GB | 2 128 758 A | 5/1984 |

(Continued)

OTHER PUBLICATIONS

International Search Report and Written Opinion for Application No. PCT/FR2010/000734 dated Mar. 30, 2011.
(Continued)

*Primary Examiner* — David A Rogers
(74) *Attorney, Agent, or Firm* — Alston & Bird LLP

(57) ABSTRACT

A device for measuring the activity of a liquid in a complex medium and an associated method, the device comprising a sealed enclosure in which the complex medium is intended to be placed and means for maintaining this enclosure at a constant temperature T, characterized in that it comprises: a means (14) for modifying the total volume of the enclosure; a pressure sensor (22) for measuring the total pressure in the enclosure; and means (24) for calculating the activity of the liquid in the complex medium from the temperature T, from the total volume of the enclosure and from the total pressure in the enclosure.

10 Claims, 2 Drawing Sheets

(56) References Cited

U.S. PATENT DOCUMENTS

| | | | |
|---|---|---|---|
| 3,309,912 A * | 3/1967 | Boland et al. | 73/38 |
| 3,574,281 A * | 4/1971 | Casey et al. | 374/55 |
| 3,635,078 A * | 1/1972 | Wissa | 73/790 |
| 3,779,085 A * | 12/1973 | Rice | 73/866 |
| 3,934,455 A * | 1/1976 | Harrisberger | 436/5 |
| 4,408,489 A * | 10/1983 | Spangle | 73/866 |
| 4,561,293 A * | 12/1985 | Richards | 73/73 |
| 4,715,212 A * | 12/1987 | Johanson | 73/38 |
| 5,005,403 A * | 4/1991 | Steudle et al. | 73/61.71 |
| 5,009,512 A * | 4/1991 | Lessi et al. | 374/6 |
| 5,161,407 A * | 11/1992 | Ankeny et al. | 73/38 |
| 5,442,948 A | 8/1995 | Cowing | |
| 5,487,307 A * | 1/1996 | Landgren et al. | 73/803 |
| 5,604,297 A * | 2/1997 | Seiden et al. | 73/19.1 |
| 6,055,850 A | 5/2000 | Turner et al. | 73/38 |
| 6,289,725 B1 * | 9/2001 | Hubbell et al. | 73/73 |
| 6,527,438 B2 * | 3/2003 | Zollinger et al. | 374/56 |
| 6,718,835 B2 * | 4/2004 | Wang et al. | 73/866 |
| 6,799,471 B1 * | 10/2004 | Regimand et al. | 73/803 |
| 6,817,238 B2 * | 11/2004 | Go Boncan et al. | 73/149 |
| 7,143,653 B2 * | 12/2006 | Abdel-Hadi et al. | 73/819 |
| 7,222,519 B2 * | 5/2007 | Ekanayake | 73/73 |
| 7,240,545 B1 * | 7/2007 | Jennings | 73/149 |
| 7,257,987 B2 * | 8/2007 | O'Brien et al. | 73/23.41 |
| 7,793,552 B2 * | 9/2010 | Ng | 73/818 |
| 8,794,078 B2 * | 8/2014 | Darbe et al. | 73/803 |
| 8,800,353 B2 * | 8/2014 | Ng | 73/73 |

FOREIGN PATENT DOCUMENTS

| | | |
|---|---|---|
| WO | WO 93/08458 A1 | 4/1993 |
| WO | WO 2005/065411 A2 | 7/2005 |

OTHER PUBLICATIONS

Lozano, A. L. et al., *Water Evaporation Versus Condensation in a Hygroscopic Soil*, Transp Porous Med 80 (2009) 209-222.

Scarpa, F. et al., *A New Procedure to Measure Water Adsorption Isotherms of Porous Fibrous Materials*, J. Porous Mater 15 (2008) 451-456.

* cited by examiner

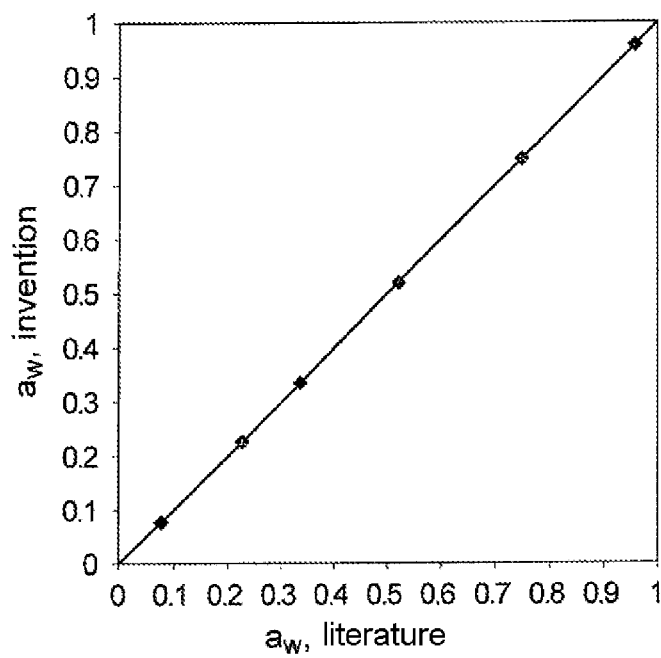
Fig.2
Fig.3
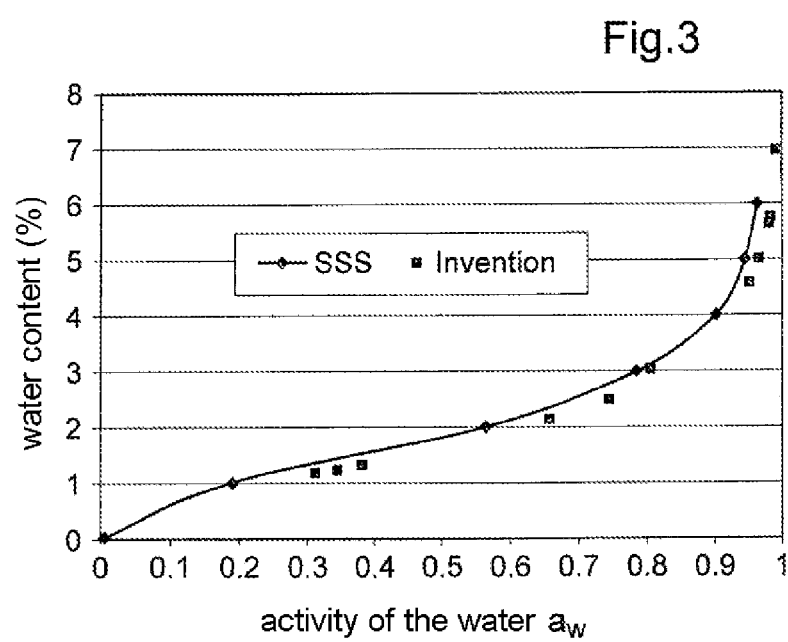

DEVICE FOR MEASURING THE ACTIVITY OF A LIQUID IN A COMPLEX MEDIUM AND ASSOCIATED METHOD

FIELD OF THE INVENTION

The present invention relates to the field of measuring the activity of a liquid in a complex medium.

BACKGROUND OF THE INVENTION

A complex medium is a medium consisting of a combination of at least a solid phase and a liquid phase, and generally including a gaseous phase, these phases being interlinked so that the volume elements containing them are separated by interfaces between phases of great extension. These interfaces of great extension modify the thermodynamic properties of the phases and the constituents forming these phases.

Depending on the nature of the solid phase, it is possible to differentiate porous media, which comprise a rigid solid structure, pastes and gels, which exhibit a deformable solid structure, powders, which exhibit a solid structure formed by an assembly of grains or even agri-foodstuff products whose solid phase retains the form of the cellular structure of the biological tissues from which they are derived.

The liquid phase is generally water, but other liquids can also be found.

When the gaseous phase is absent from the complex medium, the medium is then said to be saturated. The complex medium then comprises a solid phase and a liquid phase.

The activity of a liquid is a parameter representative of the physical-chemical bond of this liquid with the complex medium concerned, in other words, of the interaction between this liquid and this complex medium. More specifically, it is defined by the ratio between the partial vapor pressure of the liquid in the complex medium concerned and the saturating vapor pressure of the pure liquid at the same temperature.

The present invention relates in particular to the field of measuring the activity of water in a complex medium.

A device suitable for measuring the activity of water in a complex medium is applicable in the economic business sectors in which water plays an important role, for example in the agri-food industry.

In practice, such a device makes it possible to ensure the control of the quality of the products in the preparation, packaging, storage and transportation phases of food products by checking that the activity of the water does not exceed a critical value beyond which there is a risk of degradation of the products by the growth of microorganisms. Moreover, the knowledge of the activity of the water may make it possible to regulate the taste qualities or the texture of the food products.

It can also be applied in the field of powders, in particular in the pharmaceutical industry. In this case, the measurement of the activity of a liquid is representative of the bond between this liquid and the powder. This datum is of interest in controlling the agglomeration of the powder and, consequently, the production of tablets.

The field of biology and/or biotechnology may be involved. In biofiltration for example, microorganisms are used to produce molecules or to depollute the air or polluted liquids. These micro-organisms have to be kept in optimum conditions by regulating the temperature and the activity of the water for a good hydric feed.

In civil engineering, most construction materials are porous (concretes, plasters, wood). The activity of the water in these materials controls the mass transfer, which conditions the degradation of these materials over time.

In agronomy, the hydric feed to the plants is determined by the activity of the water. Below a certain activity, which depends on the plant, this feed is no longer possible. Furthermore, the chemical reactions in the soil solution which participate in the mineral feed to the plant, are closely dependent on the activity of the water. This activity is therefore an important parameter for good management of the soils.

Many other fields of application can be cited as nonlimiting examples, such as medical engineering, archeology or artwork conservation.

Devices and/or methods are known for measuring the activity of a liquid in such media.

In particular, one method that is known and widely used for measuring the activity of the water is the saturated saline solutions (SSS) method.

This method consists, first of all, in determining the desorption isotherm of a porous medium being studied. The desorption isotherm is the curve representing the trend of the water content (y axis) as a function of the trend of the activity of the water (x axis).

To this end, a sample forming a porous medium is placed in an isotherm enclosure, the sample being suspended above the saturated saline solution of the chosen salt (NaCl, KCl, KOH, etc.). The enclosure is a sealed enclosure making it possible to define an internal volume of this enclosure. In this volume, the activity is regulated precisely by the salt. The temperature is regulated by an external device.

At thermodynamic balance, that is to say, when the mass of the sample stops changing, the activity of the water in the sample is then equal to the activity of the water in the saline solution, and in the gaseous phase. By virtue of the ideal gas law applicable to water vapor, this activity is equal to the relative humidity of the humid air in the enclosure. The measurement of the partial water vapor pressure then leads to the knowledge of the activity of the water in the sample.

The water content in the sample is then measured, in order to obtain a (water content, water activity) pair.

By repeating the preceding steps with various saline solutions, it then becomes possible to establish the complete curve of the desorption isotherm. Table 1 below gives the relative humidity values at balance for different salts used—French standard NF X 15-119.

TABLE 1

| Salt | Relative humidity or activity of the water, at balance (%) |
|---|---|
| $C_2H_3KO_2$ | 22.5 |
| $CR_2Na_2O_7, 2H_2O$ | 51.7 |
| $K_2SO_4$ | 96 |
| KOH | 7.2 |
| MgCl | 33.4 |
| NaCl | 75.3 |

Once the desorption isotherm has been determined, the activity of the water in this sample can be deduced simply by measuring the water content in the sample.

One drawback with this method is that the time needed to obtain the thermodynamic balance between the saturated saline solution and the sample is lengthy, from a few days to a month when the activity of the water approaches the unity value.

Another drawback with this method is that it is indirect, in as much as it entails first determining the desorption isotherm to obtain the activity of the water in the porous medium.

Now, the determination of a single desorption isotherm does not generally represent, sufficiently accurately, the behavior of a natural medium, the latter being able to exhibit a wide variability. This variability is for example due, in the agri-food domain, to the genetic or varietal origins of the products, or to the methods used to process these products.

Another drawback with this method is that it is limited to measuring the activity of the water. This method cannot therefore relate to applications for which the measurement of the activity of a liquid other than water would be necessary. Such is, for example, the case in the environmental domain, for the depollution of soils where the measurement of the activity of a liquid other than water could make it possible to assess the stabilization of a non-aqueous pollutant (volatile organic compounds VOC, hydrocarbons, etc.).

Moreover, certain devices vary the relative humidity of the air in the enclosure, in which the sample whose activity is to be known is placed, and the sample is weighed each time. To vary the relative humidity, one known method consists, for example, in feeding the enclosure with different water vapors.

There is therefore no need to insert a new saline solution each time a measurement point is performed. Furthermore, since the thermodynamic balance is obtained more rapidly with these methods, the time needed to acquire the isotherm is shorter.

However, although these methods improve the speed of acquisition of the desorption isotherm, they are still, however, indirect and limited to measuring the activity of the water.

Moreover, they require the relative humidity to be regulated in the isotherm enclosure which can prove difficult, and generally less accurate than with the saturated saline solutions method.

To perform a regulation with an accuracy comparable to the saturated saline solutions method, consideration may be given to using devices comprising so-called "dew point" sensors. These sensors are, however, difficult to set up.

Another method for measuring the activity of the water consists in effecting temperature levels in a sealed enclosure containing the sample. The total pressure of the gaseous phase and the relative humidity of the air are measured for each level, once the thermodynamic balance is reached.

Here again, a difficulty with this type of method stems from the measurement of the relative humidity, and from the limitations of the sensor used for this purpose.

Furthermore, the method for measuring the water content that is employed (Kelvin's law) restricts the scope of the method. While this method is applicable for porous media in which the liquid is susceptible to displacement by capillarity, it cannot be used for finer porous media, such as argillaceous soils, or for media for which the liquid/gas interface does not exist, such as agri-food products or biological tissues.

SUMMARY OF THE INVENTION

One object of the invention is to propose a device for measuring the activity of a liquid, not limited to water, in a complex medium and that makes it possible to obtain this activity directly, in other words without needing to first determine the desorption isotherm of this medium.

To achieve this objective, the invention proposes a device for measuring the activity of a liquid in a complex medium, comprising a sealed enclosure in which the complex medium is intended to be placed and means for maintaining this enclosure at a constant temperature T, characterized in that it comprises:

a means for modifying the total volume of the enclosure;

a pressure sensor for measuring the total pressure in the enclosure;

a means for calculating the activity of the liquid in the complex medium, from the temperature T, the total volume of the enclosure and the total pressure in the enclosure.

The device can provide other technical features, taken alone or in combination:

a means for modifying the total volume of the enclosure is a piston which can be displaced to modify this volume, one face of said piston forming a wall of the enclosure;

the enclosure is formed by a cylinder sealed at one of its ends by a sample-holder and, at its other end, by said face of the piston;

the cylinder is mounted on rods, which are in turn mounted on a baseplate of the device;

the sample-holder is mounted on a base, which is in turn mounted on the baseplate;

it comprises means for displacing the piston in the cylinder, for example of screw/nut type;

it comprises a graduated drum to identify the position of the piston in the cylindrical tube;

it comprises a sump arranged inside the sample-holder.

To achieve this objective, the invention also proposes a method for measuring the activity of a liquid in a complex medium, characterized in that it comprises the steps consisting, after having placed the complex medium in a sealed enclosure, temperature isotherm T, in:

(a) performing a basic increment $\Delta v_j$ of the enclosure volume;

(b) after having reached the thermodynamic balance between the complex medium and the enclosure, maintaining the total pressure $p_i$, measured in the enclosure;

(c) determining a relationship (R1) between the total pressure $p_i$, the partial liquid vapor pressure at balance $p_{veq}$ and the partial pressure of the ideal gas not being dissolved, for example air, the latter being expressed using the ideal gas law, such that the relationship (R1) is expressed:

$$p_i = p_{veq} + n_a \frac{RT}{v_i} \quad (R1)$$

in which:

R is the ideal gases constant;

$n_a$ is the number of moles of the ideal gas not being dissolved;

$v_i$ is the total volume of the enclosure, defined by the relationship:

$$v_i = v_0 + \sum_{j=1}^{i} \Delta v_j$$

with $v_o$ being the initial volume of the enclosure (d) repeating steps (a) to (c) n times, with n≥1 if the initial volume of the enclosure is known or n≥2 otherwise, to deduce therefrom the value of the partial balance vapor pressure $p_{veq}$; and (e) calculating the activity of the water $a_w$ in the complex medium by the following relationship (R2):

$$a_w = \frac{p_{veq}}{p_{vs}(T)} \quad (R2)$$

in which: $p_{vs}(T)$ is the saturating vapor pressure of the pure liquid at the temperature T.

The method for measuring the activity of the liquid in the complex medium can provide a step (d) consisting in repeating the steps (a) to (c) at least 5 times.

BRIEF DESCRIPTION OF THE DRAWINGS

Other features, objectives and advantages of the invention will be stated in the following detailed description, given with reference to the appended figures, in which:

FIG. 1, which comprises

FIG. 2 represents the measurements of the activity of the water in the sample obtained, on the one hand by the device of FIG. 1 and on the other hand by the reference saturated saline solutions method, for which the data is taken from the literature (table 1), FIG. 3 represents the trend of the water content w of a sample as a function of the activity of the water $a_w$ of this sample on the one hand, with the method implemented with the device of FIG. 1 and on the other hand with the reference saturated saline solutions method.

DESCRIPTION OF THE DEVICE ACCORDING TO THE INVENTION

Figure 1A:
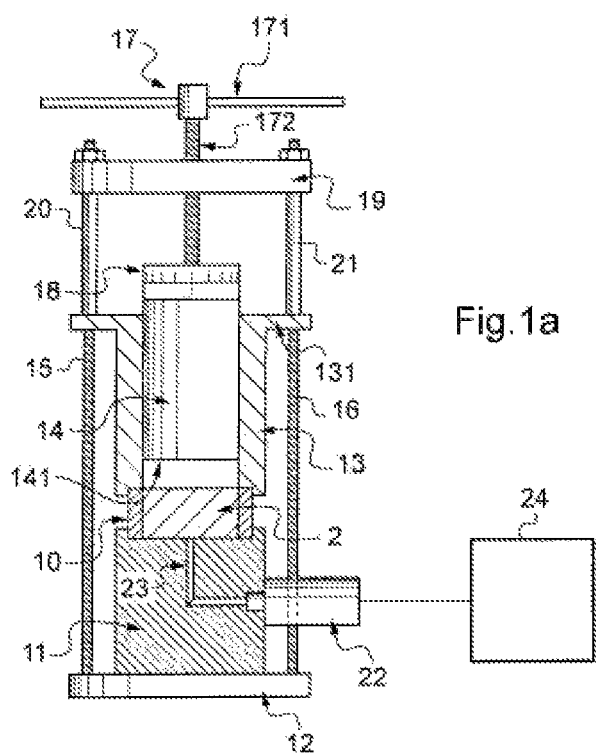
FIGS. 1(a) and 1(b), represents a device according to the invention in longitudinal cross-sectional view, FIG. 1(a) more specifically relating to the device comprising a sample-holder suitable for receiving a sample within which the activity of a liquid has to be determined, FIG. 1(b) representing a variant embodiment for which a sump is provided, arranged in the sample-holder.

The experimental device 1 represented in FIG. 1(a) comprises a sample-holder 10 in which a sample 2 comprises a liquid for which the activity is to be determined.

The sample-holder 10 is itself placed on a base 11, the latter being mounted on a baseplate 12 of the device with a diameter greater than that of the base 11.

Above the sample-holder 10, a tube of cylindrical form 13 is provided, inside which a piston 14 can be displaced.

The cylinder 13 comprises a collar 131 at the level of its top end. Rods 15, 16 hold the cylinder 13 in position by this collar 131. To this end, the rods 15, 16 are also mounted on the baseplate 12 of the device 1 and ensure the axial positioning of the cylinder 13.

The leak-tightness between the sample-holder 10, the cylinder 13 and the base 11 is ensured by o-ring seals (not represented).

The piston 14 is displaced inside the cylinder 13 by means of a system of screw-nut type 17, the screw 171 of which implements a threaded rod 172.

The threaded rod 172 is guided by a guide 19. The guide 19 is mounted on the collar 131 of the cylinder 13, via rods 20, 21. The guide 19 is thus held in position relative to the cylinder 13 and, consequently, relative to the baseplate 12 and to the base 11.

A graduated drum 18 makes it possible to identify the position of the piston 14 in the cylinder 13.

A pressure sensor 22 is mounted on the base 11, and linked to the enclosure via a fluidic channel 23. The enclosure is formed by the cylinder 13, the piston 14, one face 141 of which seals a first end of the enclosure and the sample-holder 10 sealing the other end of the enclosure. The enclosure is therefore a sealed enclosure making it possible to define an internal volume. The pressure sensor 22 makes it possible to measure the pressure inside the enclosure.

The device 1 also comprises means (not represented) for maintaining a constant temperature in the enclosure.

Table 2 below gives an example of the characteristics that can be retained for the device 1. Since the device 1 is an experimental device, these dimensions are supplied as an indication and do not prejudge the dimensions likely to be employed for a commercial device.

TABLE 2

| | |
|---|---|
| Diameter of the piston 14 | 44.5 mm |
| Maximum travel of the piston 14 | 120 mm |
| Travel of the piston 14 for one turn of the screw 172 | 1.75 mm |
| Variation of the volume of the enclosure for one turn of the screw | 2.722 cm$^3$ |
| Volume of the sample-holder 10 | 12.07 cm$^3$ |
| Accuracy of the pressure sensor 22 | 40 Pa |

Figure 1B:
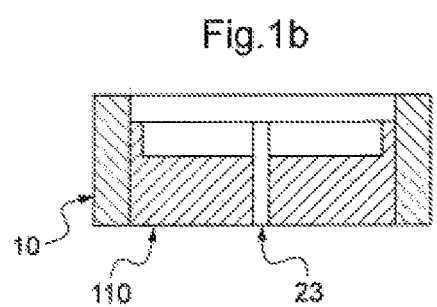

It is possible to arrange a sump 110 in the sample-holder 10, as represented in FIG. 1(b). This sump 110 can thus be used to contain various products, such as powders, pastes or gels. In this case, the fluidic channel 23 passes through the sump 110 over its entire height so that the pressure in the enclosure is transmitted to the pressure sensor 22.

Description of the Method Implemented with the Device According to the Invention With the device described previously, a sample forming a complex medium is thus placed in the isotherm enclosure (temperature T) of the device. The volume of the enclosure (internal volume) can vary with the displacement of the piston 14. With the initial state of the piston 14 in the cylinder 13, it is possible to associate a corresponding initial volume $v_o$ of the enclosure.

The initial volume $v_o$ includes the volume of the enclosure and the volumes of the pores of the complex medium that are not occupied by a liquid, but by a gas. Generally, the value of the initial volume $v_o$ is not known in as much as the volume of the sample 2 which is not occupied by the liquid but by a gas is not known.

Based on these conditions, the method for measuring the activity of the liquid in the sample 2 is as follows.

A basic increment $\Delta v_j$ of the volume of the enclosure is performed by displacing the piston 14. This volume increment is determined from reading the graduated drum, which supplies the number of screw turns, and from the conversion to be made between the number of screw turns and the volume variation. In the context of the tests described here, each increment $\Delta v_j$ corresponds to two screw turns, which corresponds to $\Delta v_j = 5$ cm$^3$ approximately (see table 2). It should also be noted that this increment can be adjusted to the sample being studied, its value being able to be increased or reduced according to the quantity of liquid present in the sample in order not to produce significant variations of the liquid content in the sample.

The enclosure is filled with a gas consisting of an ideal gas that is not dissolved, for example air, and the liquid vapor in balance with the liquid water contained in the sample 2. The total pressure in the enclosure, which is the total pressure of the gaseous phase, corresponds to the sum of the partial pressure of the air and of the partial pressure of the liquid vapor.

After having reached the thermodynamic balance between the vapor phase of the liquid contained in the sample and its liquid phase, the measurement of the total pressure in the enclosure, denoted $p_i$ for an increment i is then retained with the pressure sensor 22.

The thermodynamic balance is reached when the total pressure displayed continuously on a display screen (not represented) stops changing. Preferably, a criterion is applied concerning the relative variation of pressure between two successive measurements, a variation below which the thermodynamic balance is considered to be reached. For example, it may be accepted that the thermodynamic balance is reached when the pressure variation between two successive measurements is of the order of the precision of the pressure sensor 22, i.e. 100 Pa with the experimental device used.

By applying the ideal gas law to the air contained in the enclosure, the total pressure in the enclosure $p_i$ is then expressed $$p_i = p_{veq} + n_a \frac{RT}{v_i} \quad (R1)$$

in which:
$p_{veq}$ is the partial liquid vapor pressure at balance (Pa);
$n_a$ is the number of moles of the ideal gas not being dissolved, for example air, contained in the enclosure (mol);
R is the constant of the ideal gases (J·mol$^{-1}$·K$^{-1}$);
T is the absolute temperature in the enclosure (K); and
$v_i$ is the total volume of the enclosure (m$^3$).
The total volume $v_i$ of the enclosure is defined by the relationship:

$$v_i = v_0 + \sum_{j=1}^{i} \Delta v_j$$

in which j is the index of the number of volume increments applied.

In the relationship (R1), the values of the total pressure $p_i$ and of the temperature T of the enclosure are known, as is the enclosure volume increment value $\Delta v_j$.

On the other hand, the values of the partial liquid vapor pressure at balance $p_{veq}$ and of the number of moles, in the enclosure, of ideal gas not being dissolved are not known. In the tests described here, the nature of the sample is such that this initial volume $v_o$ cannot be directly known, so it forms an additional unknown.

For this reason, it is necessary to perform the preceding steps a number n of times such that n≥2. This makes it possible to obtain three relationships from the relationship R1, and to deduce therefrom these three unknowns. Preferably, and to increase the accuracy of the method, more volume increments can be made, for example between 6 and 8.

DETAILED DESCRIPTION OF THE INVENTION

The partial liquid vapor pressure at balance $p_{veq}$ depends only on the water content w of the sample 2. It can also be assumed that the water content w of the sample 2 varies little throughout the measurement.

This assumption is justified by the differences in density between the water in liquid form and in vapor form.

For example, at 30° C., the density of the saturating water vapor is 0.035 kg/m$^3$. Thus, for an enclosure whose volume is approximately 30 cm$^3$, the quantity of water vapor evaporated is approximately 10$^{-3}$ g, or of the order of the uncertainty of the accuracy balances employed to perform the measurement of the water content of the complex medium. Thus, if 6 volume increments are made, each volume increment can make approximately 5 cm$^3$ without modifying the water content of the sample.

Moreover, this assumption is also verified hereinafter in the description, by the comparison of the results supplied by the device according to the invention to a reference.

Therefore, the partial liquid vapor pressure at balance $p_{vi}$ can be considered to be the partial liquid vapor pressure at balance $p_{veq}$ for the liquid content w considered. It is identical throughout the measurement of the liquid activity in the sample 2.

An accurate value of the partial liquid vapor pressure at balance $p_{veq}$ is thus obtained, for the liquid content w considered.

The activity of the water $a_w$ in the sample 2 is then deduced from the following relationship:

$$HR = \frac{p_{veq}}{p_{vs}(T)} = a_w \quad (R2)$$

in which:
HR is the relative humidity of balance of the ideal gas not being dissolved, for example air, in the enclosure; and
$P_{vs}(T)$ is the saturating vapor pressure of the pure liquid at the temperature T of the enclosure.

In effect, at thermodynamic balance, the activity of the water $a_w$ in the sample 2 corresponds to the relative humidity HR of balance of the air in the enclosure.

The calculations made when implementing the method are implemented by a computation means 24, such as a computer. This makes it possible, knowing the temperature T of the enclosure, the basic volume increment of the enclosure $\Delta v_j$ and the total pressure $p_i$ supplied by the pressure sensor 22, to calculate the balance pressure $p_{veq}$ then the activity of the liquid $a_w$ in the sample 2.

For example, if 6 volume increments are made, the system of equations obtained is resolved by the least squares method, the calculation being stopped when the 6 equations of the system are satisfied to within 10$^{-4}$. This gives a very high degree of accuracy in determining $v_o$, $p_{veq}$ and $n_a$.

When the computation means 24 is a computer and in the context of the embodiment represented in FIG. 1, the temperature T of the enclosure and the volume increment of the enclosure $\Delta v_j$ can be introduced by the operator directly in the computer 24, the total pressure of the enclosure being received directly by the computer 24.

Obviously, a more refined device could be provided which required no operator intervention.

Description of the Tests Carried Out
1$^{st}$ Test

To validate the accuracy of the measurements of the activity of the water $a_w$ in the sample 2, the Applicant performed comparative tests in relation to the reference saturated saline solutions method (standard NF X 15-1 19).

The results are presented in FIG. 2, where the activity of the water $a_w$ in the sample 2 obtained by the saturated salts method is represented on the x axis and the activity of the water $a_w$ in the sample 2 obtained by the method according to the invention is represented on the y axis.

A very close match in the results obtained by the two methods can be seen.

$2^{nd}$ Test

The Applicant has determined the desorption isotherm of an argillaceous loamy soil (SLA) with the device according to the invention, and compared it to the isotherm established by the reference saturated saline solutions method (SSS).

The method implemented with the device according to the invention is therefore the one described previously, but this time repeating the steps described a number of times with samples comprising different water contents, and this is done in order to obtain a complete curve of the sorption/desorption isotherm. In reality, the sample 2 has therefore undergone neither sorption nor desorption, each sample having been prepared with a given water content w, the content being different from one sample to another.

On the other hand, with the reference saturated saline solutions method, a test performed with a desorption of such a sample was represented.

For the remainder, the conditions of implementation of the two methods are the same (temperature of the enclosure, nature of the sample concerned, etc.).

The results obtained are represented in FIG. 3.

The results obtained by the two methods are very close. The slight difference observed between the trend of the two curves is explained by the fact that the samples have not undergone any sorption/desorption with the method according to the invention. Now, those skilled in the art know that there is a hysteresis depending on whether a sorption or a desorption of a sample is performed.

Although the sorption curve likely to be obtained with the saturated saline solutions method is not represented in FIG. 3, it would easy for those skilled in the art to observe that the curve obtained with the method according to the invention is situated between the desorption curve and the sorption curve obtained with the saturated saline solutions method.

The method according to the invention is therefore accurate and can be compared, on this point, to the reference saturated saline solutions method.

Moreover, in addition to the fact that it requires no consumables, the method according to the invention offers a number of advantages.

In effect, it is much faster than the saturated saline solutions method. The thermodynamic balance is obtained in a few hours, regardless of the value of the activity of the water in the porous medium concerned. As a reminder, the time needed to obtain this thermodynamic balance with the saturated saline solutions method is several days, and can be as long as almost a month for a water activity tending towards unity.

This advantage is particularly appreciable in biological applications, for which the porous medium concerned may degrade rapidly.

Moreover, the method according to the invention is direct, in as much as it does not require the prior determination of the desorption isotherm, since the determination of the partial balance pressure $p_{veq}$ deduced from the measurements performed via the relationship (R1) make it possible to calculate the activity of the water $a_w$, via the relationship (R2).

Furthermore, the device employed to implement the method according to the invention is particularly simple in its mechanical construction and its regulation. It also requires only one pressure, and possibly temperature, sensor.

The method according to the invention does not implement regulation of the humidity of the air in the enclosure, or even measure this relative humidity, but is based on the measurement of the partial balance pressure $p_{veq}$ for the water content w considered, the activity of the liquid $a_w$ being deduced via the relationship R2.

Consequently, it is possible to determine the activity of liquids other than water. In effect, the partial balance pressure of other liquids in the enclosure can be measured with the device according to the invention.

One application that can be envisaged is that of soil pollution, for example by volatile organic compounds (VOC).

More generally, the device according to the invention can measure the activity of a liquid not only in porous media, but also in media such as powders, pastes or gels.

In the case where the complex medium is a saturated medium, the initial volume $v_o$ is limited to just the volume of the enclosure and can be known by performing a measurement by a means provided for this purpose (not represented). Consequently, the equation R1 has no more than two unknowns, which are the partial liquid vapor pressure at balance $p_{veq}$ and the number of moles $n_a$ of ideal gas not being dissolved, contained in the enclosure. Since the initial volume of the enclosure $v_o$ is known, the step (d) of the method then consists in repeating the steps (a) to (c) of this method n times, with n≥1.

The device according to the invention comprises a piston which can be displaced inside the cylinder 13 to vary the volume of the enclosure. Those skilled in the art will, however, understand that any other means for varying this volume can be envisaged.

Finally, it should be noted that the device can be used to perform a measurement other than that of the activity of a liquid in a complex medium. Thus, the device can be used to measure the partial vapor pressure of a pure liquid.

The invention claimed is:

1. A device for measuring the activity of a liquid in a complex medium, comprising a sealed enclosure, said enclosure being also an isotherm enclosure which is therefore capable of maintaining this enclosure at a constant temperature T and in which the complex medium is intended to be placed, wherein the device comprises:
    a means for modifying the total volume of the enclosure;
    a pressure sensor for measuring the total pressure in the enclosure;
    a means for calculating the activity of the liquid in the complex medium, from the temperature T of the enclosure, the total volume of the enclosure and the total pressure in the enclosure.

2. The device for measuring the activity of a liquid in a complex medium as claimed in claim 1, in which the means for modifying the total volume of the enclosure is a piston which can be displaced to modify this volume, one face of said piston forming a wall of the enclosure.

3. The device for measuring the activity of a liquid in a complex medium as claimed in claim 2, in which the enclosure is formed by a cylinder sealed at one of its ends by a sample-holder and, at its other end, by said face of the piston.

4. The device for measuring the activity of a liquid in a complex medium as claimed in claim 3, in which the cylinder is mounted on rods, which are in turn mounted on a baseplate of the device.

5. The device for measuring the activity of a liquid in a complex medium as claimed in claim 4, in which the sample-holder is mounted on a base, which is in turn mounted on the baseplate.

6. The device for measuring the activity of a liquid in a complex medium as claimed in claim 3, in which means are provided to displace the piston in the cylinder.

7. The device for measuring the activity of a liquid in a complex medium as claimed in claim 3, in which a graduated drum is provided to identify the position of the piston in the cylindrical tube.

8. The device for measuring the activity of a liquid in a complex medium as claimed in claim 3, in which a sump is provided, arranged inside the sample-holder.

9. A method for measuring the activity of a liquid in a complex medium, wherein the method comprises the steps consisting, after having placed the complex medium in a sealed enclosure, said enclosure being also an isotherm enclosure which is therefore capable of maintaining this enclosure at a constant temperature T, in:
  (a) performing a basic increment $\Delta v_j$ of the enclosure volume;
  (b) after having reached the thermodynamic balance between the complex medium and the enclosure, maintaining the total pressure $p_i$, measured in the enclosure;
  (c) determining a relationship (R1) between the total pressure $p_i$, the partial liquid vapor pressure at balance $p_{veq}$ and the partial pressure of the ideal gas not being dissolved, for example air, the latter being expressed using the ideal gas law, such that the relationship (R1) is expressed:

$$p_i = p_{veq} + n_a \frac{RT}{v_i} \quad (R1)$$

in which:
R is the ideal gases constant;
$n_a$ is the number of moles of the ideal gas not being dissolved;
$v_i$ is the total volume of the enclosure, defined by the relationship:

$$v_i = v_0 + \sum_{j=1}^{i} \Delta v_j$$

with $v_o$ being the initial volume of the enclosure
  (d) repeating steps (a) to (c) n times, with n>1 if the initial volume of the enclosure is known or n>2 otherwise, to deduce therefrom the value of the partial balance vapor pressure $p_{veq}$; and
  (e) calculating the activity of the liquid $a_w$ in the complex medium by the following relationship (R2):

$$a_w = \frac{p_{veq}}{p_{vs}(T)} \quad (R2)$$

in which:
$p_{vs}(T)$ is the saturating vapor pressure of the pure liquid at the temperature T.

10. The method for measuring the activity of a liquid in a complex medium as claimed in claim 9, in which the step (d) consists in repeating the steps (a) to (c) at least 5 times.

* * * * *